US012774483B2

(12) United States Patent
Kwon et al.

(10) Patent No.: US 12,774,483 B2
(45) Date of Patent: Oct. 27, 2026

(54) BIOSENSOR STRUCTURE FOR MEASURING SPECIMEN AND METHOD FOR MEASURING SPECIMEN BY USING THE SAME

(71) Applicant: DONG WOON ANATECH CO., LTD., Seoul (KR)

(72) Inventors: Min Su Kwon, Seoul (KR); Ji Won Kye, Seoul (KR); Hee Jae Woo, Seoul (KR); Eun Hyun Shim, Seoul (KR); In Su Jang, Seoul (KR); Dong Cheol Kim, Seoul (KR)

(73) Assignee: DONG WOON ANATECH CO., LTD, Seoul (KR)

(*) Notice: Subject to any disclaimer, the term of this patent is extended or adjusted under 35 U.S.C. 154(b) by 954 days.

(21) Appl. No.: 17/777,376

(22) PCT Filed: Sep. 28, 2021

(86) PCT No.: PCT/KR2021/013243
§ 371 (c)(1),
(2) Date: Nov. 7, 2022

(87) PCT Pub. No.: WO2022/065986
PCT Pub. Date: Mar. 31, 2022

(65) Prior Publication Data

US 2023/0057549 A1 Feb. 23, 2023

(30) Foreign Application Priority Data

Sep. 28, 2020 (KR) .......................... 1020200125618
Aug. 10, 2021 (KR) .......................... 1020210105599

(51) Int. Cl.
*C12Q 1/00* (2006.01)
*C12Q 1/32* (2006.01)

(52) U.S. Cl.
CPC ............... *C12Q 1/006* (2013.01); *C12Q 1/32* (2013.01)

(58) Field of Classification Search
CPC ... A61B 5/145; A61B 5/1486; A61B 10/0051; C12Q 1/006; C12Q 1/32; G01N 27/3271; G01N 27/3272; G01N 27/3273
See application file for complete search history.

(56) References Cited

U.S. PATENT DOCUMENTS 7,556,723 B2 * 7/2009 Funke ................ G01N 27/3272 204/403.02
8,888,972 B2 * 11/2014 Lee .................... G01N 27/3272 204/403.02

(Continued)

FOREIGN PATENT DOCUMENTS

JP 05505459 8/1993
JP 09068533 3/1997

(Continued)

OTHER PUBLICATIONS

International Search and Written Opinion with English Translation, International Application No. PCT/KR2021/013243, Jan. 12, 2022, mailing date of search report, Jan. 12, 2022.

(Continued)

*Primary Examiner* — Charles Capozzi
*Assistant Examiner* — Dwayne K Handy
(74) *Attorney, Agent, or Firm* — Foley & Lardner LLP

(57) ABSTRACT

Disclosed are a biosensor structure for sample measurement and a sample measuring method using same. In a biosensor electrode structure for sample measurement according to an embodiment of the present invention, a working electrode, which is an electrode for measuring a sample, and a reference electrode are arranged to be spaced apart from each other in the longitudinal direction of a sample insertion channel, a working protrusion, which is a protrusion of the (Continued)

working electrode, and two reference protrusions, which are protrusions of the reference electrode, are alternately arranged at a part corresponding to the sample insertion channel, the ratio of the area of the working protrusion to the areas of the reference protrusions is equal to or greater than 1, at least one recognition electrode for recognizing the sample is disposed adjacent to the working electrode or the reference electrode and parallel to the working electrode and the reference electrode while being spaced apart from the working electrode and the reference electrode, and the at least one recognition electrode has at least one recognition protrusion which is a protrusion disposed at the part corresponding to the sample insertion channel.

10 Claims, 4 Drawing Sheets

(56) References Cited

U.S. PATENT DOCUMENTS

| | | | | |
|---|---|---|---|---|
| 2003/0146110 | A1* | 8/2003 | Karinka ............ | G01N 27/3272 204/403.01 |
| 2005/0016844 | A1* | 1/2005 | Burke ............... | G01N 27/3272 204/403.01 |
| 2011/0272295 | A1 | 11/2011 | Lee et al. | |

FOREIGN PATENT DOCUMENTS

| | | | |
|---|---|---|---|
| JP | 2001021527 | A | 1/2001 |
| JP | 2007521484 | A | 8/2007 |
| JP | 2008-544234 | | 12/2008 |
| JP | 2010-525373 | | 7/2010 |
| JP | 2014-206516 | | 10/2014 |
| JP | 2015-092198 | | 5/2015 |
| JP | 2017037067 | A | 2/2017 |
| KR | 1020090081762 | A | 7/2009 |
| KR | 1020100042399 | A | 4/2010 |
| KR | 1020180004386 | A | 1/2018 |
| KR | 1020180072509 | A | 6/2018 |
| KR | 1020200062944 | A | 6/2020 |
| WO | WO-02/08743 | | 1/2002 |
| WO | 2006137549 | A1 | 12/2006 |

OTHER PUBLICATIONS

Translated Indian Office Action, App. No. 202317008844, dated Jan. 12, 2024, pp. 1-12.

Translated Japanese Office Action, Application No. 2023-519395, dated Mar. 5, 2023, pp. 1-18.

* cited by examiner

| Glucose concentration (uM) | 0 | 100 | 250 | 500 | 1000 |
|---|---|---|---|---|---|
| Measure Current (nA) | 1870 | 2247 | 2510 | 3280 | 4909 |

BIOSENSOR STRUCTURE FOR MEASURING SPECIMEN AND METHOD FOR MEASURING SPECIMEN BY USING THE SAME

TECHNICAL FIELD

The inventive concept relates a biosensor structure for measuring a specimen, and a technology for measuring a specimen by using the same, and ore particularly, to a biosensor structure that may improve a measurement accuracy for glucose included in a specimen, for example, saliva, and a method for measuring the specimen by using the same.

BACKGROUND ART

It is chemically or clinically important to quantitatively or qualitatively analyze a target material that is present in a bio sample. For example, representative examples thereof include measuring glucose in blood for diabetes patients or measuring cholesterol that causes various adult diseases.

As known in the field, it is very important to measure activation of enzymes, from a bio sample (hereinafter, will be referred to as "a specimen"), for example, a specific material in saliva or blood, for example, by using a glucose sensor, a uric acid sensor, a protein sensor, or a DNA sensor in a clinical/chemical inspection, and glutamate-oxaloacetate transaminase (GOT) or glutamate-pyruvate transaminase (GPT) in a liver function inspection more rapidly and with reproducibility. Here, the biosensor includes an identification part that identifies a measurement target and a conversion part for conversion to an electrical signal.

A bio material is used for the identification part, and when the bio material recognizes a target, it is chemically or physically changed. A part that converts the change into an electrical signal is a change part, and the identification part and the conversion part are generally called biosensor electrodes.

In a measurement method of a biosensor of a currently commercialized strip type, it is general to introduce a specimen into a specimen insertion passage of the biosensor by using a capillary phenomenon that causes a force that is stronger than the gravitational force of the earth, which is allowed through a plasma or chemical interface surface activity processing process in a manufacturing process thereof, accumulate the specimen in the specimen insertion passage, and measure the specimen qualitatively or quantitatively.

Then, generally, prior to the measurement of the specimen, an operation of detecting a specimen introduction time point that is a time point, at which the specimen is introduced and is accumulated in the specimen insertion passage.

Conventionally, a scheme of detecting a specimen introduction time point by applying a specimen introduction detection signal to a working electrode and a reference electrode and measuring a specimen by applying a specimen measurement signal to the working electrode and the reference electrode after lapse of a specific period of time. That is, the specimen introduction is determined by temporally calculating a time point, at which a passage capacity formed by inserting the specimen is completely reached with respect to a time point, at which the specimen reaches the working electrode and the reference electrode, and the specimen is measured by applying the specimen measurement signal to the working electrode and the reference electrode again after waiting a predetermined period of time thereafter.

In this case, an electric double layer (EDL) is formed as the specimen introduction detection signal applied to detect the specimen introduction time point reacts surfaces of the working electrode and the reference electrode that are important as measurement electrodes in advance. Here, the electric double layer appears at a border of different materials (the electrode, the specimen, or a solution), and may be caused when an electric field is applied to surfaces, on which different materials contact each other. An electric double layer capacitance (DLC) that is a capacitance of the electric double layer may include, even though a fine amount, a current signal measured when the specimen detection signal is applied. Accordingly, the measurement signal of the biosensor is distorted so that the measurement result may be influenced.

Furthermore, when the specimen is measured by temporally calculating a period of time, from the introduction time point of the specimen to deposition of the specimen in the passage and waiting for a predetermined period of time, the viscosities of the specimens are different, so that even though a fine amount, the result may become different according to a speed or a period of time for which the specimen is deposited in the passage and is influenced by the specimen. Accordingly, an accuracy of the measurement may become considerably problematic when a time point, at which the specimen measurement signal is applied, is determined by using a temporal control.

DISCLOSURE

Technical Problem

Embodiments of the inventive concept provide a method for measuring a specimen, by which a measurement accuracy for glucose included in the specimen, for example, saliva may be improved, and a method for measuring a specimen by using the same.

Embodiments of the inventive concept provide a system for measuring a specimen, by which a measurement accuracy for a material included in the specimen may be improved by measuring the specimen through a biosensor after collecting the specimen and removing interference materials that are obstructions in measuring the specimen from the collected specimen.

Technical Solution

According to an aspect of the inventive concept, there is provided a biosensor electrode structure for measuring a specimen, wherein a working electrode and a reference electrode that are electrodes for measuring the specimen are spaced apart from each other in a lengthwise direction of a specimen insertion passage, wherein a working boss that is a boss of the working electrode and reference bosses that are two bosses of the reference electrode are alternately arranged in a part corresponding to the specimen insertion passage, and a ratio of an area of the working boss and an area of the reference bosses is 1 or more, wherein at least one recognition electrode for recognizing the specimen is disposed adjacent to the working electrode or the reference electrode and is spaced apart from the working electrode and the reference electrode in parallel, and wherein a recognition boss that is at least one boss is disposed in a part of the at least one recognition electrode, which corresponds to the specimen insertion passage.

The recognition boss may be disposed to be adjacent to a distal end of the specimen insertion passage.

The at least one recognition electrode may recognize the specimen in response to a specimen recognition signal applied independently from a specimen measurement signal applied to the working electrode and the reference electrode.

The biosensor electrode structure may further include a strip recognition electrode that detects a moment, at which a biosensor including the electrode structure is inserted into a measurer for measurement.

According to an aspect of the inventive concept, there is provided a biosensor structure for measuring a specimen, the biosensor structure including a lower plate, in which a working electrode and a reference electrode that are electrodes for measuring a specimen, and at least one recognition electrode for recognizing the specimen are disposed in an insulation substrate, the working electrode and the reference electrode are spaced apart from each other in a lengthwise direction of a specimen insertion passage, a working boss that is a boss of the working electrode and reference bosses that are two bosses of the reference electrode are alternately arranged in a part corresponding to the specimen insertion passage, and a ratio of an area of the working boss and an area of the reference bosses is 1 or more, at least one recognition electrode is disposed adjacent to the working electrode or the reference electrode and is spaced apart from the working electrode and the reference electrode in parallel, and a recognition boss that is at least one boss is disposed at a part corresponding to the specimen insertion passage, a middle plate having the specimen insertion passage, wherein an enzyme compound is inserted into the specimen insertion passage, and an upper plate, in which an insertion hole for inserting the specimen and a discharge hole for discharging air are formed at parts of an insulation substrate, which correspond to the specimen insertion passage.

The enzyme compound may, when the specimen is saliva, include an enzyme for causing a selective reaction of glucose included in the saliva, a polymer for attaching the enzyme onto the electrodes disposed in the lower plate, a catalyst for expediting a reaction of the enzyme and the glucose, and the enzyme may include 1 unit to 30 units of at least one of glucose oxidase and glucose dehydrogenase (GDH), the polymer may include 0.01 wt % to 1.0 wt % of at least one of chitosan, PVP, nafion, polyethylene glycol, poly vinyl pyrrolidone, poly vinyl alcohol, agarose, and trehalose, and the catalyst may include 1% to 10% of at least one of Ferrocene, a Ferrocene derivative, Quinone, a Quinone derivative, hexamine ruthenium (III) chloride, and a ferricyanide.

The catalyst may include 0.001% to 5% of Prussian blue.

The at least one recognition electrode may recognize the specimen in response to a specimen recognition signal applied independently from a specimen measurement signal applied to the working electrode and the reference electrode.

According to an aspect of the inventive concept, there is provided a system for measuring a specimen, the system including a collection device including a collection unit that collects a specimen, and a filter that removes interference materials that are obstructions in measuring the specimen collected by the collection unit, a biosensor having an electrode structure, in which a working electrode and a reference electrode that are electrodes for measuring the specimen, from which the interference materials have been removed, and at least one recognition electrode for recognizing the specimen, from which the interference materials have been removed, are disposed in an insulation substrate, the working electrode and the reference electrode are spaced apart from each other in a lengthwise direction of a specimen insertion passage, a working boss that is a boss of the working electrode and reference bosses that are two bosses of the reference electrode are alternately arranged in a part corresponding to the specimen insertion passage, and a ratio of an area of the working boss and an area of the reference bosses is 1 or more, at least one recognition electrode is disposed adjacent to the working electrode or the reference electrode and is spaced apart from the working electrode and the reference electrode in parallel, and a recognition boss that is at least one boss is disposed at a part corresponding to the specimen insertion passage, and a measurement device that, when the specimen, from which the interference materials have been removed through the collection device, is inserted into the biosensor after a strip of the biosensor is inserted, measures the specimen, from which the interference materials have been removed, based on a specimen measurement signal received through the working electrode and the reference electrode.

When the specimen is saliva, the filter may remove big molecular materials and foreign substances, which are present in the saliva, and may separate proteins, amylase, and ions that are obstructions in measuring sugar in the saliva.

The biosensor may include a lower plate having the electrode structure, a middle plate having the specimen insertion passage, wherein an enzyme compound is inserted into the specimen insertion passage, and an upper plate, in which an insertion hole for inserting the specimen, from which the interference materials have been removed, and a discharge hole for discharging air are formed at parts corresponding to the specimen insertion passage.

The enzyme compound may, when the specimen is saliva, include an enzyme for causing a selective reaction of glucose included in the saliva, a polymer for attaching the enzyme onto the electrodes disposed in the lower plate, and a catalyst for expediting a reaction of the enzyme and the glucose, the enzyme may include 1 unit to 30 units of at least one of glucose oxidase and glucose dehydrogenase (GDH), the polymer may include 0.01 wt % to 1.0 wt % of at least one of chitosan, PVP, nafion, polyethylene glycol, poly vinyl pyrrolidone, poly vinyl alcohol, agarose, and trehalose, and the catalyst may include 1% to 10% of at least one of ferrocene, a ferrocene derivative, Quinone, a Quinone derivative, hexamine ruthenium (III) chloride, and a ferricyanide.

The catalyst may include 0.001% to 5% of Prussian blue.

According to an aspect of the inventive concept, there is provided a method for measuring a specimen, the method including collecting a specimen by using a collection unit, and removing interference materials that are obstructions in measuring the specimen, from the collected specimen, by using a filter, causing the specimen, from which the interference materials have been removed, to contact a biosensor, and measuring a response signal to the specimen, from which the interference materials have been removed, by applying a specimen measurement signal to a working electrode and a reference electrode of the biosensor, when a contact of the specimen, from which the interference materials have been removed, is recognized by at least one recognition electrode of the biosensor, wherein the working electrode and the reference electrode are spaced apart from each other in a lengthwise direction of a specimen insertion passage, a working boss that is a boss of the working electrode and reference bosses that are two bosses of the reference electrode are alternately arranged in a part corresponding to the specimen insertion passage, and a ratio of an area of the working boss and an area of the reference bosses is 1 or more, and at least one recognition electrode is disposed adjacent to the working electrode or the reference electrode and is spaced apart from the working electrode and the reference electrode in parallel, and a recognition boss that is at least one boss is disposed in a part corresponding to the specimen insertion passage.

Advantageous Effects

According to the embodiments of the inventive concept, a measurement accuracy for a material included in the specimen may be improved by measuring the specimen through a biosensor after collecting the specimen, for example, saliva and removing interference materials that are obstructions in measuring the specimen from the collected specimen.

According to the embodiments of the inventive concept, a measurement accuracy for sugar of saliva may be improved by measuring saliva, from which interference materials have been removed, through a biosensor provided with an enzyme compound after removing the interference material that are obstructions in measuring the saliva by using a filter.

DESCRIPTION OF DRAWINGS

The above and other objects and features will become apparent from the following description with reference to the following figures, wherein like reference numerals refer to like parts throughout the various figures unless otherwise specified, and wherein.

BEST MODE

Figure 1:
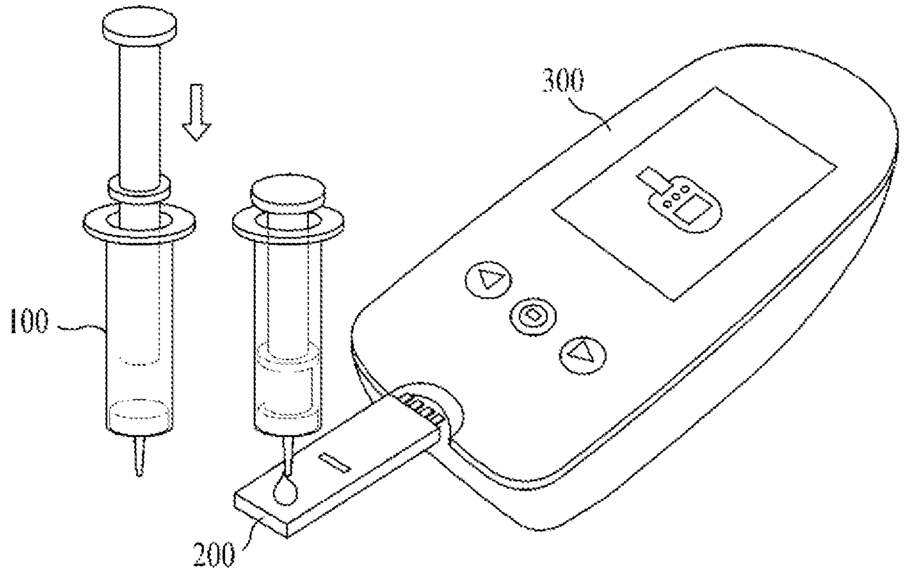
FIG. 1 illustrates an exemplary view illustrating a system for measuring a specimen according to the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprising" and/or "comprises" used in the specification mean that the mentioned elements, steps, operations, and/or devices do not exclude existence or addition of one or more other elements, steps, operations, and/or devices.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, preferred embodiments of the inventive concept will be described in detail with reference to the accompanying drawings. The same elements on the drawings will be denoted by the same reference numerals, and a description of the same elements will not be repeated.

Embodiments of the inventive concept provide a biosensor that may improve a measurement accuracy for a material included in a specimen, by collecting the specimen, for example, saliva, removing interference materials that are obstructions in measuring the collected specimen, and measuring glucose included in the saliva through the biosensor, and a system for measuring a specimen by using the same.

Here, when the specimen is saliva, the filter may remove big molecular materials and foreign substances, which are present in the saliva, and may separate proteins, amylase, and ions that are obstructions in measuring sugar in the saliva.

In the biosensor, a working electrode and a reference electrode that are electrodes for measuring a specimen, and at least one recognition electrode for recognizing the specimen are disposed, the working electrode and the reference electrode are spaced apart from each other in a lengthwise direction of a specimen insertion passage, a boss (hereinafter, will be referred to as "a working boss") of the working electrode and two bosses (hereinafter, will be referred to as "reference bosses") of the reference electrode are alternately arranged in a part corresponding to the specimen insertion passage, and a ratio of an area of the working boss and an area of the reference bosses is 1 or more, at least one recognition electrode for recognizing the specimen is disposed adjacent to the working electrode or the reference electrode and is spaced apart from the working electrode and the reference electrode in parallel, and at least one boss (hereinafter, will be referred to as "a recognition boss") is disposed in a part of the at least one recognition electrode, which corresponds to the specimen insertion passage.<0}

Then, an electrode structure of the biosensor may further include a strip recognition electrode for detecting a moment, at which a biosensor is inserted into a measurer for measurement.

In the biosensor, an enzyme compound may be inserted into a middle plate having the specimen insertion passage, and the enzyme compound may include an enzyme, a polymer, and a catalyst.

Then, when the specimen is saliva, the enzyme may cause a selective reaction of glucose included in the saliva, the polymer may be for attaching the enzyme onto the electrodes disposed in the biosensor, and the catalyst may be for expediting a reaction of the enzyme and the glucose.

The inventive concept will be described below with reference to FIGS. 1 to 6.

FIG. 1 illustrates an exemplary view illustrating a system for measuring a specimen according to the inventive concept. As illustrated in FIG. 1, a system 100 for measuring a specimen according to an embodiment of the inventive concept includes a collection device 110, a biosensor 200, and a measurement device 300.

Figure 2:
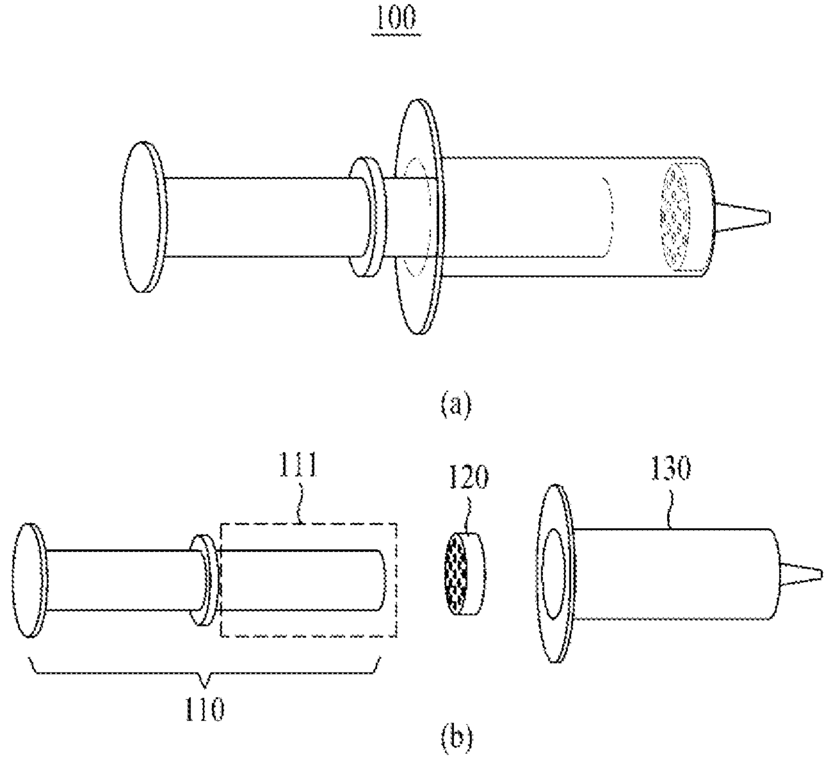
FIG. 2 illustrates a configuration of an embodiment of a collection device illustrated in FIG. 1.

The collection device 100, as illustrated in FIG. 2, includes a specimen collecting unit 110 including a specimen collecting swab 111 for collecting a specimen, a filter 120, ad a compression tube 130.

Then, when the specimen is saliva, the specimen collecting unit 110 may collect saliva through the specimen collecting swab 111, and the saliva collected by the specimen collecting unit 110 may be provided to an outside, that is, the biosensor 200 after the interference materials included in the saliva is removed through the filter 120 inserted into the compression tube 130.

That is, when the collection device 100 collects the saliva and the specimen collecting unit 110 is compressed in a direction of the compression tube 130 in the compression tube 130, the interference materials included in the collected saliva may be removed through the filter 120, and big molecular materials and foreign substances, which are present in the saliva, may be removed and material that are obstructions, such as proteins, amylase, and ions, in measuring sugar in the saliva may be separated.

The filter 120 may include at least one layer. Of course, in the filter 120 of the inventive concept, an additional material may be added to the above-described materials in consideration of a removal degree of the interference materials, which are to be removed from the specimen, and thicknesses of the manufactured layers may become different. Furthermore, when the filter 120 includes a plurality of layers, layers manufactured of different materials may be sequentially stacked to form the filter.

The biosensor 200 is adapted to perform a function of sensing information that is to be measured from the specimen, from which the interference materials have been removed, for example, glucose when the specimen collected by the collection device 100 is inserted through the collection device 100, and recognizes the specimen based on a specimen recognition signal received from the measurement device 300 after the biosensor strip 200 is inserted into the measurement device 300, and provides a response signal to glucose included in the specimen to the measurement device 300 through the specimen measurement signal applied separately from the specimen recognition signal.

Figure 3:
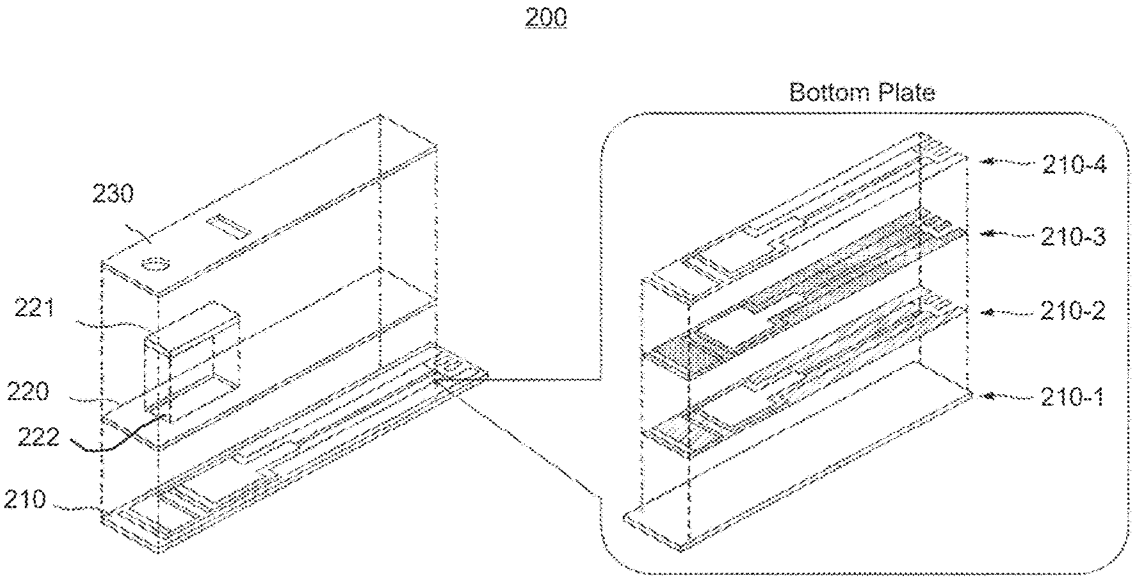
FIG. 3 illustrates an exemplary view of a biosensor structure illustrated in FIG. 1.
Figure 4:
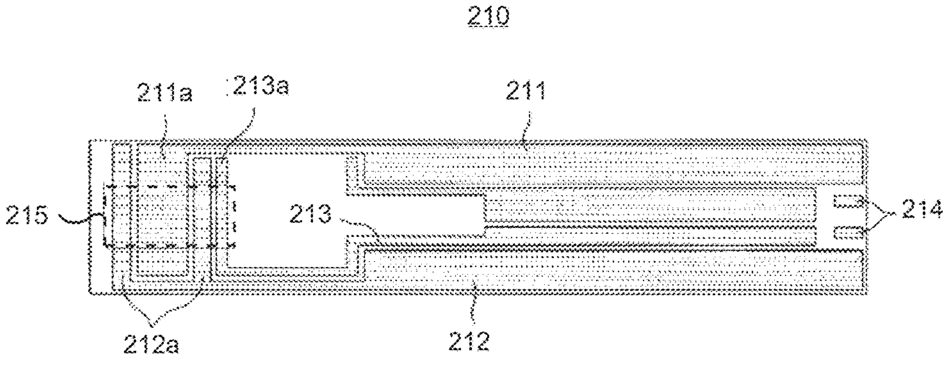
FIG. 4 illustrates an exemplary view of a biosensor electrode structure illustrated in FIG. 3.

The biosensor 200, as illustrated in FIG. 3, may include an upper plate 230, a middle plate 220, and a lower plate 210, and as illustrated in FIG. 4, the biosensor electrode structure is formed in the lower plate 210.

In detail, the specimen insertion passage 222 is formed in the middle plate 220, and an enzyme compound 221 may be inserted into the specimen insertion passage.

Here, the specimen insertion passage is apparent to an ordinary person in the art, and a detailed description thereof will be omitted.

The enzyme compound 221 may include an enzyme for causing a selective reaction of glucose included in the saliva, a polymer for attaching the enzyme onto the electrodes disposed in the lower plate, and a catalyst for expediting a reaction of the enzyme and the glucose.

Then, the catalyst may include 1% to 10% of at least one of ferrocene, a ferrocene derivative, Quinone, a Quinone derivative, hexamine ruthenium (III) chloride, and a ferricyanide, and the enzyme may include 1 unit to 30 units of at least one of glucose oxidase and glucose dehydrogenase (GDH), and the polymer may include 0.01 wt % to 1.0 wt % of at least one of chitosan, PVP, nafion, polyethylene glycol, poly vinyl pyrrolidone, poly vinyl alcohol, agarose, and trehalose.

The upper plate 230 is formed on an upper side of the middle plate 220, and in the upper plate 230, an insertion hole for inserting the specimen collected through the collection device and a discharge hole for discharging air are formed at parts of an insulation substrate, which correspond to the specimen insertion passage.

In the lower plate 210, a working electrode 211 and a reference electrode 212 that are electrodes for measuring a specimen, and at least one recognition electrode 213 for recognizing the specimen are disposed in the insulation substrate 211, the working electrode 211 and the reference electrode 212 are spaced apart from each other in a lengthwise direction of the specimen insertion passage, a working boss 211*a* of the working electrode 211 and two reference bosses 212*a* of the reference electrode 212 are alternately arranged at a part 215 corresponding to the specimen insertion passage, and a ratio of an area of the working boss 211 and an area of the reference bosses 212 is 1 or more, the at least one recognition electrode 213 may be disposed adjacent to the working electrode 211 or the reference electrode 212 to be spaced apart from the working electrode 211 and the reference electrode 212 in parallel, and an electrode structure, in which at least one recognition boss 213*a* is disposed in a part 215 corresponding to the specimen insertion passage, is provided.

Here, the lower plate 210 may be formed as a plurality of metal layers having an electrode structure overlap each other. For example, the lower plate 210 may be formed as a first metal layer 210-2 of copper having a biosensor electrode structure on an insulation substrate 210-1, a second metal layer 210-3 of nickel, and a third metal layer 210-4 of gold overlap each other.

Moreover, the biosensor electrode structure, as illustrated in FIG. 4, may further include a strip recognition electrode 214 that detects whether the biosensor strip is inserted in the measurement device, into a part, into which the biosensor strip is inserted into the measurement device.

Furthermore, while the working electrode 211 and the reference electrode 212 are spaced apart from each other in a lengthwise direction of the specimen insertion passage, a width of the electrode in a part in a direction of the measurement device 300 is wider than a width of the electrode in a part of the specimen insertion passage, and the one working boss 211*a* is disposed between the two reference bosses 212*a* to be alternately arranged. Then, because the area of the working boss 211*a* is at least larger than the area of the two reference bosses 212*a*, a measurement accuracy of the specimen may be increased. That is, because the sugar of the saliva is lower than the sugar of the blood, the response signal to the specimen measurement signal may be accurately measured to improve a measurement accuracy of the sugar of the saliva when the saliva contacts the working boss 211*a* by making the area of the working boss 211*a* larger.

Furthermore, when the recognition electrode 213 is disposed between the reference electrode 212 and the working electrode 211, the recognition boss 213*a* may be formed at a distal end of the specimen insertion passage.

An interval between the working boss 211*a* and the reference boss 212*a*, an interval between the reference boss 212*a* and the recognition boss 213*a*, and the widths of the bosses may be determined in consideration of the measurement accuracy of the specimen, and may be determined by a person or a service provider that provides the technology.

Because the recognition electrode 214 receives the specimen recognition signal for recognizing the specimen from the measurement device 300 when the biosensor strip is inserted into the measurement device 300, the measurement device 300 may recognize the specimen through the response signal to the specimen recognition signal.

When the biosensor strip 200 is inserted into the measurement device 300, the reference electrode 212 and the working electrode 211 also may receive the specimen measurement signal for measuring the specimen from the measurement device 300, the specimen measurement signal may be received separately from the specimen recognition signal, and a time point, at which the specimen measurement signal is received, may be a time point, at which the biosensor strip 200 is inserted into the measurement device 300, and may be a time point, at which the specimen is recognized by the recognition electrode 213. Of course, the measurement device 300 may recognize whether the biosensor strip 200 is inserted through the strip recognition electrode 214 provided in the biosensor strip 200.

The specimen measurement signal applied to the reference electrode 212 and the working electrode 211 are signals corresponding to a specific electric potential between the reference electrode 212 and the working electrode 211, and the specimen measurement signal may be applied to the reference electrode and the working electrode by applying preset different voltages.

When the biosensor strip 200 is inserted, the measurement device 300 recognizes that the biosensor strip 200 is inserted through the strip recognition electrode 214 provided in the biosensor strip 200, provides the specimen recognition signal to the recognition electrode 213 of the biosensor, provides the specimen measurement signal to the reference electrode 212 and the working electrode 211, when it is determined that the specimen contacts the biosensor after determining whether the specimen contacts the biosensor, receives a response signal to the specimen that is to be measured, and measures the specimen.

Here, when the specimen is the saliva, the measurement device 300 may measure the sugar of the saliva.

Furthermore, the measurement device 300 may provide a measured result value on the sugar of the saliva, through a display unit, or may additionally provide a color on a degree of glucose.

Figure 5:
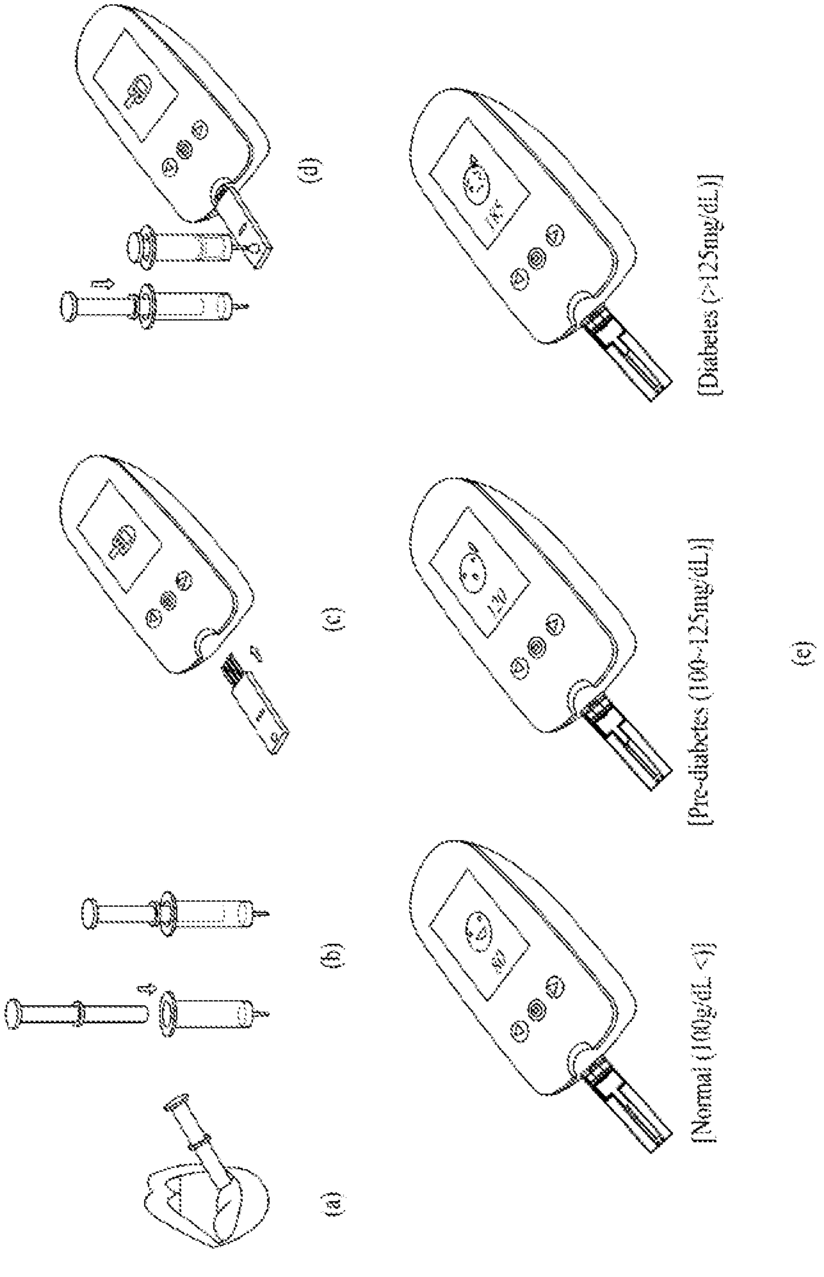
FIG. 5 illustrates an exemplary view illustrating a method for measuring a specimen according to the inventive concept.

FIG. 5 illustrates an exemplary view illustrating a method for measuring a specimen according to the inventive concept. A process of measuring the sugar of the saliva will be described as follows.

Referring to FIG. 5, in a description of a method of measuring the specimen, as illustrated in FIGS. 5A and 5B, after collecting the saliva of a target by using the specimen collecting unit of the collection device, the specimen collecting unit is inserted into the compression tube provided with the filter.

Furthermore, as illustrated in FIGS. 5C and 5D, after the biosensor strip having the biosensor electrode structure of the inventive concept is inserted into the measurement device, the interference materials are filtered out or removed from the saliva collected by the collection unit, through the compression of the collection device and the saliva is inserted into the insertion hole of the biosensor.

Then, the measurement device may provide the specimen recognition signal to the recognition electrode of the biosensor by recognizing that the biosensor has been inserted, and ma provide the specimen measurement signal to the reference electrode and the working electrode when the saliva is inserted into the insertion hole and is recognized.

When the specimen measurement signal is applied to the electrodes of the biosensor, as illustrated in FIG. 5E, a response signal to the specimen measurement signal is received and a measurement result for the response signal is provided through the display unit.

Here, the measurement result provided through the display unit may provide results of several stages according to a measurement value, and the value ranges and the result according to the sugar of the saliva are apparent to an ordinary person in the art, and a detailed description thereof will be omitted.

In this way, in the biosensor, the system for measuring the specimen, and the method for measuring the specimen according to the embodiments of the inventive concept, a measurement accuracy for the material included in the specimen, for example, the saliva may be improved by collecting the specimen, removing the interference materials that are obstructions in measuring the specimen, from the collected specimen, and measuring glucose included in the saliva through the biosensor.

Furthermore, in the biosensor, the system for measuring the specimen, and the method for measuring the specimen according to the embodiments of the inventive concept, a measurement accuracy for the sugar of the saliva may be improved by removing the interference materials that are obstructions in measuring the sugar of the saliva by using the filter, and measuring the saliva, from which the interference materials have been removed, through the biosensor provided with the enzyme compound.

Figure 6:
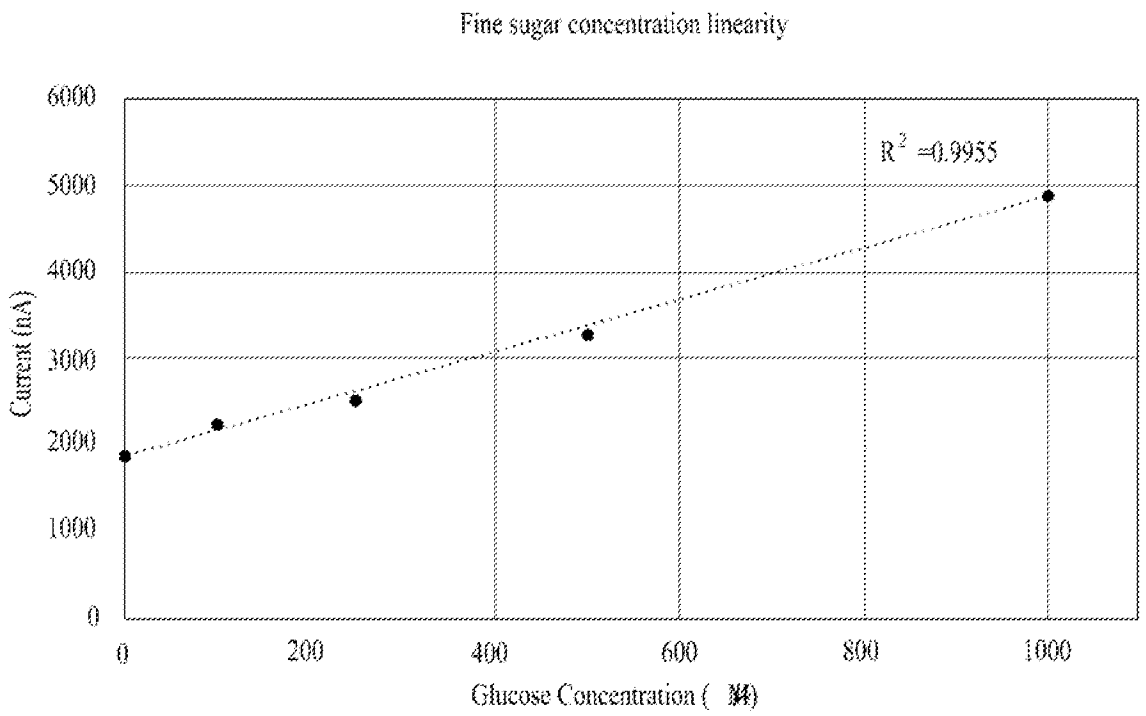
FIG. 6 is a view illustrating an experimental graph, in which fine sugar concentrations are measured by the system for measuring a specimen according to the inventive concept.

In particular, in the biosensor, the system for measuring the specimen, and the method for measuring the specimen according to the embodiments of the inventive concept, the enzyme compound includes the enzyme, in which 1 unit to 30 units of at least one of glucose oxidase and glucose dehydrogenase (GDH) is used, the polymer, in which 0.01 wt % to 1.0 wt % of at least one of chitosan, PVP, nafion, polyethylene glycol, poly vinyl pyrrolidone, poly vinyl alcohol, agarose, and trehalose is used, and the catalyst, in which 1% to 10% of at least one of ferrocene, a ferrocene derivative, Quinone, a Quinone derivative, hexamine ruthenium (III) chloride, and a ferricyanide is used (the catalyst may include 0.001% to 5% of Prussian blue when the Prussian blue is used), whereby, as illustrated in FIG. 6, a concentration of the sugar may be finely measured.

The above-described apparatus may be realized by a hardware element, a software element, and/or a combination of a hardware element and a software element. For example, the apparatus and the elements described in the embodiments, for example, may be realized by using one or more general-purpose computer or a specific-purpose computer such as a processor, a controller, an arithmetic logic unit (ALU), a digital signal processor, a microcomputer, a field programmable array (FPA), a programmable logic unit (PLU), a microprocessor, or any device that may execute and respond to an instruction. The processing device may perform an operation system and one or more software applications performed on the operating system. Further, the processing device may access, data, manipulate, process, and produce data in response to execution of software. Although one processing device is used for convenience of understanding, it may be easily understood by those skilled in the art that the processing device may include a plurality of processing elements and/or a plurality of types of processing elements. For example, the processing device may include a plurality of processors or one processor and one controller. Further, another processing configuration, such as a parallel processor, may be possible.

The software may include a computer program, a code, an instruction, or a combination of one or more thereof, and the processing device may be configured to be operated as desired or commands may be made to the processing device independently or collectively. The software and/or data may be permanently or temporarily embodied in any type of machine, a component, a physical device, virtual equipment, a computer storage medium or device, or a signal wave transmitted in order to be interpreted by the processing device or to provide an instruction or data to the processing device. The software may be dispersed on a computer system connected to a network, to be stored or executed in a dispersive method. The software and data may be stored in one or more computer readable recording media.

The method according to the embodiment may be implemented in the form of a program instruction that maybe performed through various computer means, and may be recorded in a computer readable medium. The computer readable medium may include a program instruction, a data file, and a data structure alone or in combination thereof. The program instruction recorded in the medium may be designed or configured particularly for the embodiment or may be a usable one known to those skilled in computer software. An example of the computer readable recording medium may include magnetic media such as a hard disk, a floppy disk, and a magnetic tape, optical recording media such as a CD-ROM and a DVD, magneto-optical media such as a floptical disk, and hardware devices that are particularly configured to store and perform a program instruction, such as a ROM, a RAM, and a flash memory. Further, an example of the program instruction may include high-level language codes which may be executed by a computer using an interpreter as well as machine languages created by using a compiler.

Although the embodiments of the present disclosure have been described with reference to the limited embodiments and the drawings, the present invention may be variously corrected and modified from the above description by those skilled in the art to which the present invention pertains. For example, the above-described technologies can achieve a suitable result even though they are performed in different sequences from those of the above-mentioned method and/or coupled or combined in different forms from the method in which the constituent elements such as the system, the architecture, the device, or the circuit are described, or replaced or substituted by other constituent elements or equivalents.

Therefore, the other implementations, other embodiments, and the equivalents of the claims pertain to the scope of the claims.

What is claimed is:

1. A biosensor for measuring saliva glucose in saliva, comprising:

a lower plate including a plurality of electrodes for measuring the saliva glucose;

a middle plate arranged on the lower plate and having a specimen insertion passage, wherein an enzyme compound which reacts with the saliva is located in the specimen insertion passage to measure the saliva glucose; and an upper plate arranged on the middle plate, wherein the upper plate includes an insertion port for inserting the saliva which is formed in a region corresponding to the specimen insertion passage, and a discharge port for discharging air which is formed in another region different from the region, wherein the lower plate comprises:

a first electrode and a second electrode for measuring the saliva glucose, wherein the first electrode includes a first body part and at least one first electrode boss, and the second electrode includes a second body part and a plurality of second electrode bosses, at least one third electrode for detecting insertion of the saliva through the specimen insertion passage, wherein the third electrode includes a third body part and at least one third electrode boss, and an insulation substrate on which the first electrode, the second electrode, and the third electrode are disposed, wherein at least a portion of the at least one first electrode boss, at least a portion of the plurality of second electrode bosses, and at least a portion of the at least one third electrode boss are located in a part of the lower plate corresponding to specimen insertion passage and is configured to receive the saliva which is inserted through the specimen insertion passage, wherein the at least one first electrode boss and the plurality of second electrode bosses are spaced apart from each other in a lengthwise direction of the part of the lower plate corresponding to the specimen insertion passage, wherein the at least one first electrode boss and the plurality of second electrode bosses are alternately arranged in the part of the lower plate corresponding to the specimen insertion passage, wherein the at least one third electrode boss is disposed adjacent to the at least one first electrode boss or the plurality of second electrode bosses, and is disposed to be in parallel with and spaced apart from the at least one first electrode boss and the plurality of second electrode bosses, wherein a quantity of the at least one first electrode boss is less than a quantity of the plurality of second electrode bosses, and wherein an area of each of the at least one first electrode boss is different from an area of each of the plurality of second electrode bosses.

2. The biosensor of claim 1, wherein the area of each of the at least one first electrode boss is larger than the area of each of the plurality of second electrode bosses.

3. The biosensor of claim 1, wherein the first electrode and the second electrode are respectively a working electrode and a reference electrode.

4. The biosensor of claim 1, wherein a quantity of the at least one first electrode boss which overlaps with the enzyme compound in a direction perpendicular to the lengthwise direction is less than a quantity of the plurality of second electrode bosses which overlap with the enzyme compound in the direction perpendicular to the lengthwise direction, and wherein an area of each of the at least one first electrode boss which overlaps with the enzyme compound in the direction perpendicular to the lengthwise direction is different from an area of each of the plurality of second electrode bosses which overlap with the enzyme compound in the direction perpendicular to the lengthwise direction.

5. The biosensor of claim 1, wherein the enzyme compound is inserted to cover beyond both ends of each of the at least one first electrode boss and the plurality of second electrode bosses along the lengthwise direction.

6. The biosensor of claim 1, wherein the first body part and the second body part are spaced apart from each other, and each of the first body part and the second body part has a width in a direction perpendicular to the lengthwise direction, and wherein each of a width of the first body part and a width of the second body part varies at least partially along the lengthwise direction.

7. The biosensor of claim 6, wherein the third body part is disposed between the first body part and the second body part, and wherein the at least one third electrode boss is disposed adjacent to an end of the part of the lower plate corresponding to the specimen insertion passage in the lengthwise direction.

8. The biosensor of claim 7, wherein the third electrode is configured to perform specimen recognition in response to a specimen recognition signal applied independently of a specimen measurement signal applied to the first electrode and the second electrode.

9. The biosensor of claim 8, wherein the lower plate further comprises a strip recognition electrode for detecting whether the biosensor is inserted into a measurement device.

10. A system for measuring saliva glucose in saliva, comprising:

a collection device comprising:

a collection unit configured to collect the saliva, and a filter configured to remove interference materials in the saliva;

the biosensor of any one of claims 1 to 9; and a measurement device configured to receive the biosensor, transmit a specimen recognition signal and a specimen measurement signal to the biosensor, and receive a response signal to the specimen recognition signal and a response signal to the specimen measurement signal from the biosensor.

* * * * *